(12) United States Patent
Preuthun

(10) Patent No.: US 6,508,788 B2
(45) Date of Patent: Jan. 21, 2003

(54) MEDICATION DELIVERY DEVICE WITH TELESCOPIC PISTON ROD

(75) Inventor: Jan Harald Preuthun, Brønshøj (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 10/032,824

(22) Filed: Oct. 25, 2001

(65) Prior Publication Data

US 2002/0107487 A1 Aug. 8, 2002

Related U.S. Application Data

(60) Provisional application No. 60/246,679, filed on Nov. 8, 2000.

(30) Foreign Application Priority Data

Oct. 27, 2000 (DK) ........................................ 2000 01608

(51) Int. Cl.⁷ ................................................ A61M 1/00
(52) U.S. Cl. ...................................... 604/152; 604/187
(58) Field of Search ................. 128/DIG. 1, DIG. 12, 128/DIG. 13; 604/68, 70, 72, 131, 151, 152, 153, 154, 155, 156, 187

(56) References Cited

FOREIGN PATENT DOCUMENTS

| WO | WO 90/09202 | 8/1990 |
|----|-------------|--------|
| WO | WO 92/10425 | 6/1992 |
| WO | WO 94/15660 | 7/1994 |
| WO | WO 97/00091 | 1/1997 |
| WO | WO 00/15280 | 3/2000 |

Primary Examiner—Manuel Mendez
(74) Attorney, Agent, or Firm—Marc Began, Esq.; Richard Bork, Esq.; Reza Green, Esq.

(57) ABSTRACT

A medication delivery device comprising a container containing a fluid medicament. The medicament is expelled from the container by moving forward an elastomeric piston inside the cartridge. The piston is moved forward by a telescopic piston rod, which can either be centrally located in the container or eccentric located. One end of the telescopic piston rod abuts the elastomeric piston either by itself or through an additional plate. The abutment having a friction large enough to prevent a lower part of the telescopic rod from rotating. In order to prevent the elastomeric piston from rotating inside the container a second telescopic piston rod is provided parallel with the first telescopic piston rod.

10 Claims, 4 Drawing Sheets

MEDICATION DELIVERY DEVICE WITH TELESCOPIC PISTON ROD

CROSS-REFERENCE TO RELATED APPLICATIONS

The present application claims priority under 35 U.S.C. §119 based on U.S. provisional patent application No. 60/246,679, filed on Nov. 8, 2000.

BACKGROUND OF THE INVENTION

The invention relates to a medication delivery device for delivering medicine or other fluent material into a mammal body.

Medication delivery devices are widely used in the health sector for delivering fluent medicine into mammal bodies through a conduit inserted in the body. In general two types of medication delivery devices exist. The first type being an injection device, which injects a selected dose of fluent medicine into a mammal body whenever the injection device is activated. The other type being an infusion device, which delivers a constant rate of medicine into a mammal body either by gravity or by pressure, which pressure are usually generated by an electrical motor.

People suffering from diabetes will require insulin to be delivered into the body either through several injections every day or through a constant infusion.

A medication delivery device for injecting pre-selected doses of fluent medicine into the body is known from WO 90.09202. The medication delivery device shown in this publication comprises a piston rod made up from an outer part and an inner part. The inner part has an exterior thread and is rotated by a drive mechanism. The outer part has an interior thread mating the thread of the inner part and is locked against rotation, such that the outer part moves forward whenever the inner part is being rotated. Since the outer part at its distal end abuts the elastomeric piston of the cartridge, this elastomeric piston is moved forward when the inner part is rotated hence expelling an amount of the medicine contained in the cartridge. In order to fully empty a cartridge the length of the outer part of the piston rod has to be at least equal to the length of the cartridge. The total length of the injection device must therefore be at least twice the length of the cartridge.

In order to produce medication delivery devices shorter than twice the length of the cartridge, a telescopic piston rod has been developed. Such a telescopic piston rod is shown, utilized in an infusion device, in WO 97.00091. This known piston rod comprises of a plurality of pieces or parts, which are connected to each other by mating threads. The distal part of the telescopic piston rod is connected to the elastomeric piston of the cartridge, and is prevented form rotating by a number of bushings surrounding the telescopic piston rod and being stiffly connected to the housing of the medication delivery device. When the drive rotates the proximal part of the telescopic piston rod, the distal part moves forward hence expelling the medicine contained in the cartridge.

SUMMARY OF THE INVENTION

If the shown telescopic piston rod has to fold and unfold correctly the bushing having the smallest diameter must surround the part of the telescopic piston rod having the largest diameter, as shown in WO 97.00091. The bushing having the smallest diameter then has to fit into at least one other bushing having a greater diameter, and finally the interior diameter of the cartridge has to be larger than the diameter of the largest bushing. As a result of this the diameter of the cartridge must be of a considerable size, especially if a long cartridge having a telescopic piston rod made up from a large number of parts is called for.

Another deficiency of the prior art medication delivery device is that the part of the largest bushing protruding out from the cartridge has to have an overall diameter equaling the interior diameter of the cartridge, leaving only a limited space in the housing for the remaining parts of the medication delivery device.

It is an object of the present invention to provide a medication delivery device, which does not posses the drawbacks of the prior art medication delivery devices, where the diameter of the cartridge is minimized, and where the non-occupied space available inside the housing is maximized.

This is obtained by a medication delivery device for delivering medicine or other fluent material to a mammal body, having a housing accommodating a cartridge containing an amount of said medicine, comprising:

an elastomeric piston movable mounted in said cartridge, which elastomeric piston is moved from a proximal end of said cartridge to a distal end of said cartridge by rotating at least a part of a first telescopic piston rod, which first telescopic piston rod has a distal part abutting said elastomeric piston and a proximal part rotatably mounted in said housing and a plurality of parts there between, said parts being connected to each other by mating threads, drive means for rotating said first telescopic piston rod, such that said elastomeric piston moves forward inside said cartridge and expels an amount of said medicine, and means preventing said elastomeric piston from rotating when said part of said first telescopic piston rod is rotated, which medication delivery device according to the invention is characterized in that said means preventing said elastomeric piston from rotating when at least a part of said first telescopic piston rod is rotated comprises an additional telescopic piston rod having a proximal end mounted in said housing and a distal end abutting said elastomeric piston.

When a telescopic piston rod is used, the elastomeric piston most be prevented from rotating in order to be advanced inside the cartridge. If an additional piston rod abutting the elastomeric piston is located in the cartridge this will effectively hinder the elastomeric piston from rotating when the first piston rod is expanded. Both piston rods can be made with a very little diameter, such that they both at the same time can fit into the interior of a standard cartridge. Since they are both fitted into the same cartridge, the addition of the diameter of both the telescopic piston rods is substantially smaller than the interior diameter of the cartridge, thereby leaving some non-occupied space both in the cartridge and in the housing of the medication delivery device.

In the present context the term 'elastomeric piston' is taken to mean a displaceable plate or cylinder that fits tightly to the inner walls of a cartridge. One surface of the elastomeric piston is in contact with the contents of the cartridge while the opposite surface is in contact with a piston rod.

The term 'piston rod' is in the present context taken to be the element which are used to apply pressure to a surface of the elastomeric piston, such that the elastomeric piston is being displaced and the contents of the cartridge is being expelled.

The term 'telescopic piston rod' is taken to mean a piston rod made up from a number of individual parts or pieces, which parts or pieces preferably has a circular cross-section, but the parts could if wanted be of any desired form. All the pieces, although the most distal part or piece could be solid, is preferably hollow thereby creating an interior compartment in each part or piece, which compartment has a diameter or a width large enough to fit the neighbouring piece into the compartment, such that the telescopic piston rod can be transformed from a position where all the pieces are contained in the compartment of the neighbouring piece to a position where all the pieces are extracted out of the compartments or almost of the compartments. In the first position the overall length of the telescopic piston rod is somewhat equal to the length of the longest part or piece, and in the extracted position the length of the telescopic piston rod almost equals the total sum of the length of each individual piece.

In the present context, the term 'abutting the elastomeric piston' or 'elastomeric piston . . . in contact with a piston rod' is taken to mean that the piston rod may or may not be fixed to the movable elastomeric piston. In both cases the piston rod has the ability to displace the elastomeric piston at least in a direction towards the outlet of the cartridge. When, as disclosed in claim 2, the additional telescopic piston rod is rotatably mounted in the housing, it is ensured that a telescopic piston rod equal to the first telescopic piston rod can be utilized as the additional telescopic piston rod.

When, as disclosed in claim 3, the additional telescopic piston rod extends parallel with the first piston rod inside said cartridge, it is ensured that the construction of the bearings can be kept simple. The bearings carrying the rotating parts of the telescopic piston rods can e.g. be ball bearings as shown or a combination of a ball bearing and a needle bearing located at the proximal end of the telescopic piston rod. If the two telescopic piston rods crosses each other inside the cartridge, or if they in any other way are kept non-parallel, the design of the bearings will be much more complicated.

When, as disclosed in claim 4 the first telescopic piston rod and said additional telescopic piston rod is connected to each other through a synchronisation gear such that both telescopic pistons rods rotates with the same rotational speed, and that one of said telescopic piston rods is rotated by an electrical motor which drives one of said telescopic piston rod through a driving gear, it is ensured that although the electrical motor only drives one of the two telescopic piston rods they are both rotated with the same rotational speed. If the pitch of the threads connecting the pieces of each telescopic piston rod is the same for both telescopic piston rods it is ensured that the distal end of each telescopic piston rod moves at the same speed. If the synchronization utilizes only two gear wheels, as shown, the first telescopic piston rod and the additional telescopic piston rod will rotate in different directions. When the two telescopic piston rods are moving in different directions, the momentum delivered to the elastomeric piston from the one telescopic piston rod being driven by the electrical motor will be equalized by the momentum delivered from the other telescopic piston rod and the resulting momentum working on the elastomeric piston will be zero. If an uneven number of gearing wheels are utilized, the two telescopic piston rods will rotate in the same direction which will build up a momentum at the point where the telescopic piston rods is secured in the housing.

In an embodiment of the medication delivery device according to the invention, the first telescopic piston rod and said additional telescopic piston rod each comprises of three parts; a first part having an interior thread, a third part having an exterior thread and an intermediate second part having an exterior thread mating said interior thread of said first part and an interior thread mating said exterior thread of said third part. Having a telescopic piston rod made up from three parts have been found to provide a length and a stability suitable for a medication delivery device When, as disclosed in claim 6, the first part of said first telescopic piston rod and said first part of said additional telescopic piston rod is located at said proximal end of said cartridge, and that said third part of said first telescopic piston rod and said third part of said additional telescopic piston rod is moving towards said distal end of said cartridge, it is ensured that the piece of each telescopic piston rod having the largest diameter and containing the other pieces of the telescopic piston rod is the piece located at the most proximal end of the medication delivery device.

The direction of the pith of the threads provided on the pieces making up each telescopic piston rod determines in which direction each telescopic piston rod moves when the first piece is being rotated. In an embodiment of the medication delivery device according to the invention, the direction of said threads of said first telescopic piston rod and said additional telescopic piston rod is such that said distal end of each telescopic piston rod travels in the same direction inside said cartridge when one of said telescopic piston rods is rotated. If as mentioned in claim 8, the first telescopic piston rod and said additional telescopic piston rod rotates in the same direction, the threads of each telescopic piston rod most be in the same direction whereas if the first telescopic piston rod and said additional telescopic piston rod rotates in opposite directions, as mentioned in claim 9, the thread of each telescopic piston rod most be in opposite directions.

When, as disclosed in claim 10, the first telescopic piston rod at said distal end is connected to said distal end of said additional telescopic piston rod preferably through a circular plate abutting said elastomeric piston inside said cartridge, it is ensured that the two telescopic piston rods are locked to each other and that the momentum is adequate balanced between the two telescopic piston rods.

BRIEF DESCRIPTION OF THE SEVERAL VIEWS OF THE DRAWINGS

The invention will be explained more fully below in connection with a preferred embodiment and with reference to the drawings in which.

The figures are schematic and simplified for clarity, and they just show details, which are essential to the understanding of the invention, while other details are left out. Throughout, the same reference numerals are used for identical or corresponding parts.

DETAILED DESCRIPTION OF THE INVENTION

Initially it may be convenient to define that, the term "distal end" of the housing 1 and of the cartridge 2 is meant to refer to the end carrying the conduit through which the medicine is expelled, whereas the term "proximal end" is meant to refer to the opposite end carrying the drive mechanism.

Figure 1:
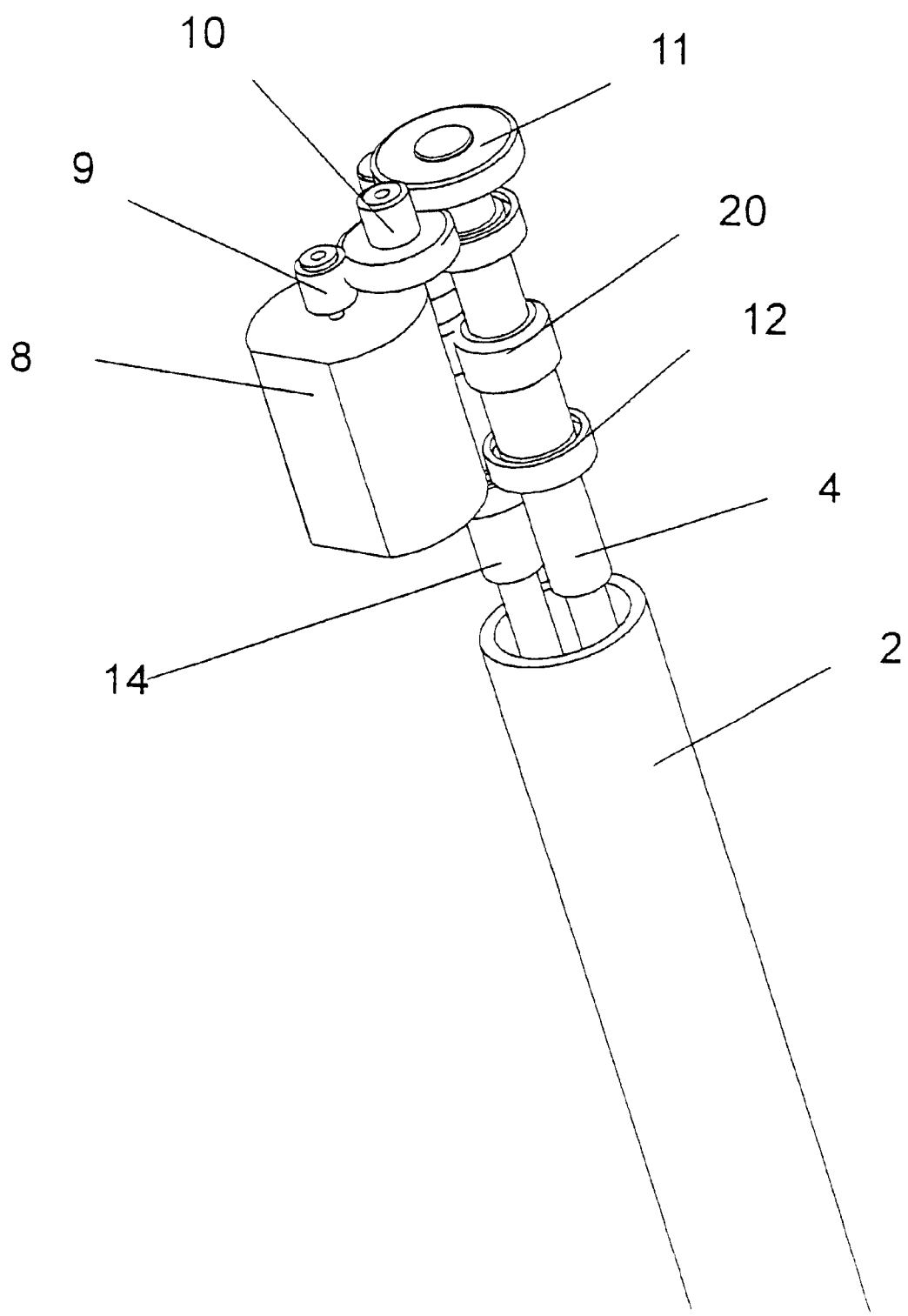
FIG. 1 Shows a perspective view of the medication delivery device according to the invention.
Figure 2:
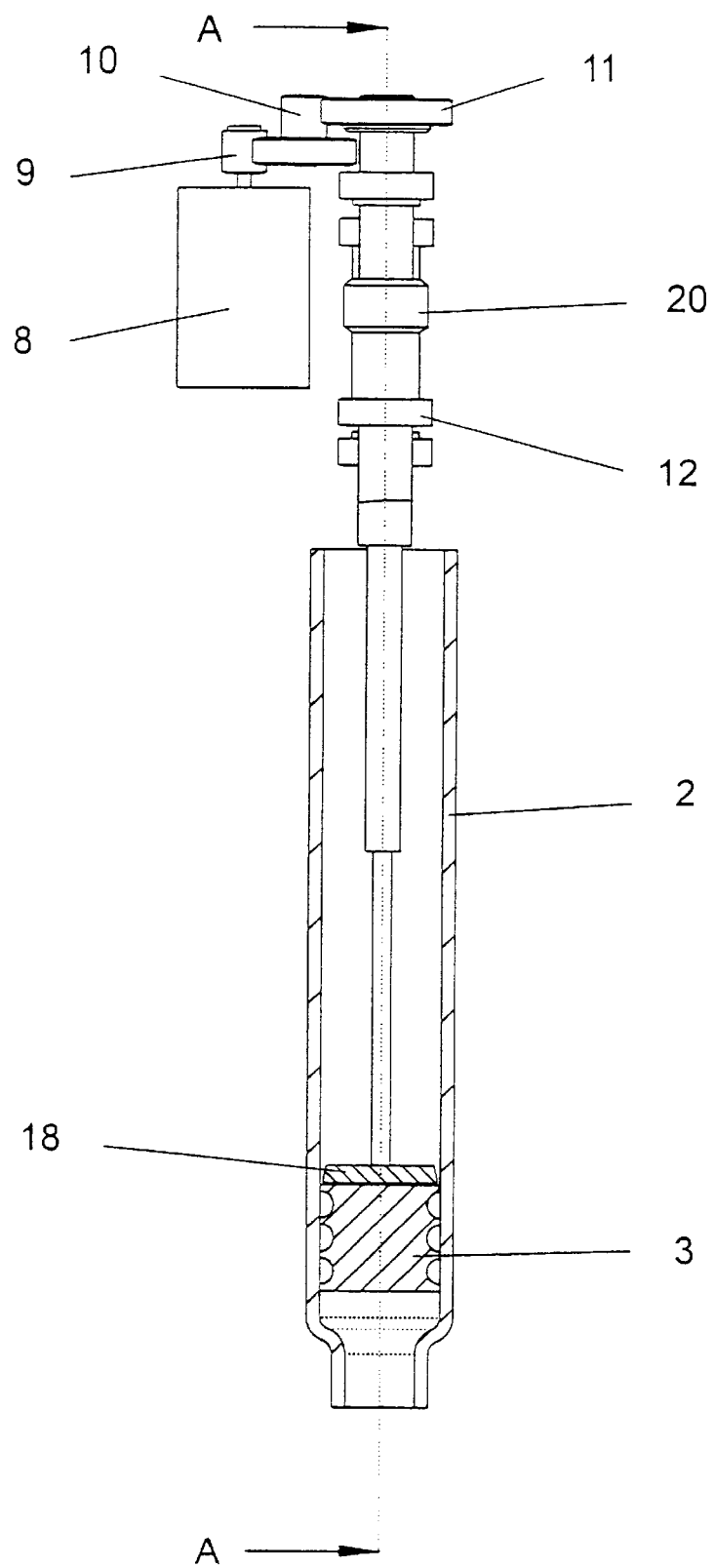
FIG. 2 Shows a sectional view along line B—B in FIG. 3.
Figure 3:
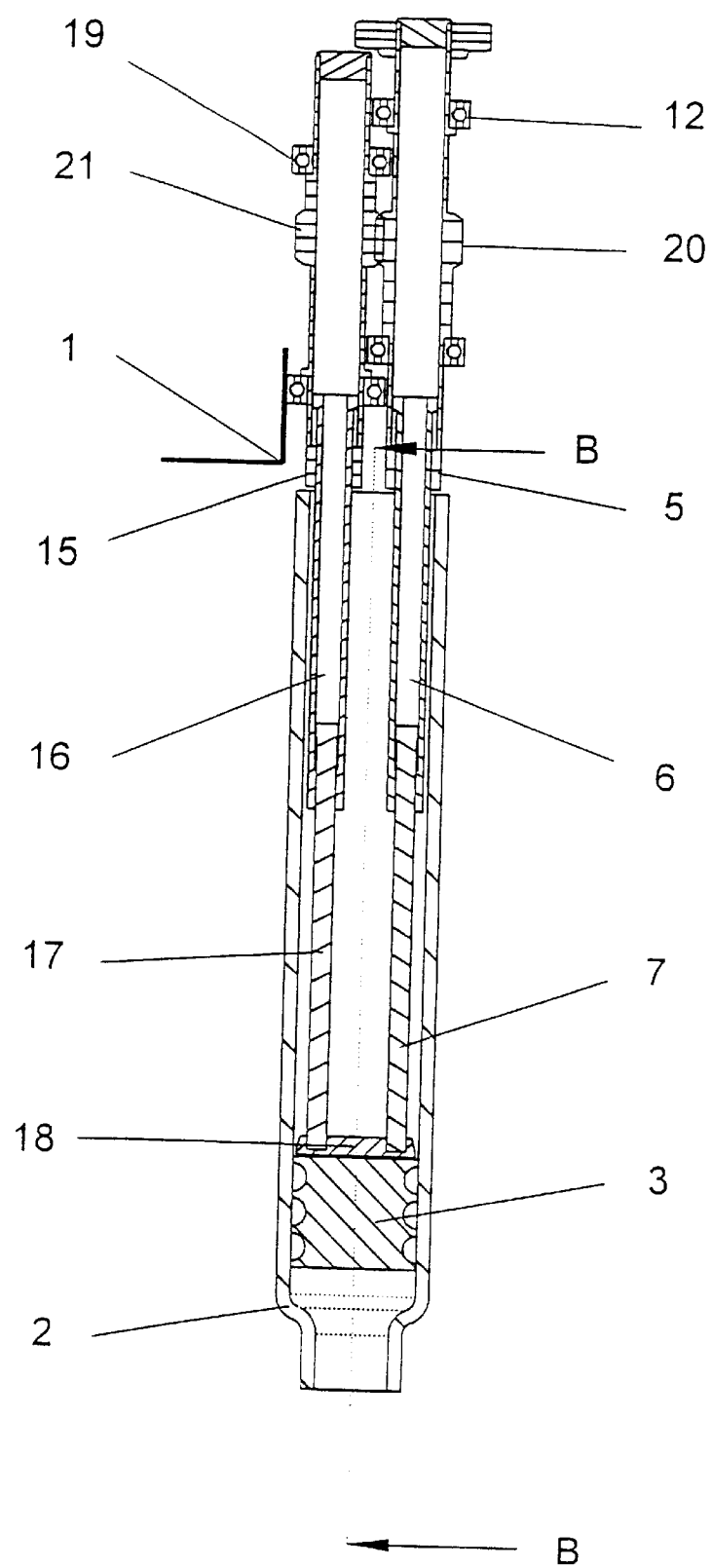
FIG. 3 Shows a sectional view along line A—A in FIG. 2.

FIGS. 1 to 3 shows a medical injection device comprising a housing 1 accommodating a cartridge 2 containing the fluent medicine to be injected. An elastomeric piston 3 is movable mounted inside the cartridge 2. The fluent medicine will be expelled when the movable elastomeric piston 3 is moved towards the distal end of the medical injection device.

The elastomeric piston 3 is moved forward by a first telescopic piston rod 4 made up from three parts 5, 6, 7. The first part 5 has an interior thread mating the exterior thread of the second intermediate part 6. The second intermediate part 6 is in addition provided with an interior thread mating the exterior thread of the third part 7. When the first part 5 is rotated, and the elastomeric piston 3 as well as the third part 7 of the first telescopic piston rod 4 is locked against rotation, the second intermediate part 6 and the third part 7 will be moved in the distal direction due to the mating threads. This will cause the elastomeric piston 3 to move in the distal direction and expel the medicine contained in the cartridge 2.

Rotating the first part 5 of the first telescopic piston rod 4 is done by an electrical motor 8 which is coupled to the first part 5 of the first telescopic piston rod 4 through a number of gearing wheels 9, 10, 11. The first part 5 of the telescopic piston rod is rotatably mounted in the housing 1 through a number of ball bearings 12. Other types of bearings can off cause be used if so wanted.

Locking the elastomeric piston 3 and the first part 5 of the telescopic piston rod 4 against rotation can be done in many different ways. In the embodiment shown in the figures the locking is realized by providing an additional telescopic piston rod 14. This additional telescopic piston rod 14 is made up in the same manner as the first telescopic piston rod 4 and comprises three parts 15, 16, 17, which is connected together by mating threads.

The third part 17 of the additional telescopic piston rod 14 is at the distal end connected to the first telescopic piston rod 4 through a circular plate 18 having a distal side abutting the elastomeric piston 3, and the first part 15 of the additional telescopic piston rod 14 is rotatably mounted in the housing 1 by a number of ball bearings 19.

The additional telescopic piston rod 14, which sole purpose is to prevent the elastomeric piston 3 and the third part 7 of the first telescopic piston rod 4 from rotating when the first part 5 of the first telescopic piston rod 4 is rotated, can either be made as a dummy slave following the longitudinal movement of the first telescopic piston rod 4, or it can be fully synchronized with the first telescopic piston rod 4.

When the additional telescopic piston rod 14 is made as a dummy slave it is preferably made without any threads and connected to the first telescopic piston rod only through the circular plate 18, or by other means only transmitting the longitudinal movement from the first telescopic piston rod 4 to the additional telescopic piston rod 14. Since only longitudinal movement is transmitted, the first part 15 of the additional telescopic piston 14 rod need not be rotational mounted in the housing 1.

When the additional telescopic piston rod 14 is synchronized with the first telescopic piston rod 4, the synchronisation can be done by providing the first telescopic piston rod 4 and the additional telescopic piston rod 14 with a synchronization gear made up from a first gear wheel 20 connected to the first telescopic piston rod 4 and a second gear wheel 21 connected to the additional telescopic piston rod 14, which two gear wheels 20,21 interconnects with each other.

If the synchronisation utilizes only two gear wheels 20, 21 interconnecting each other, the first telescopic piston rod 4 and the additional piston rod 14 will rotate in different directions, which will cause the momentum delivered from the first telescopic piston rod 4 to be equalized by the momentum delivered from the additional telescopic piston rod 14, such that the resulting momentum working on the circular plate 18 will be zero.

If the additional telescopic piston rod 14 is made as a dummy slave following the longitudinal movement of the first telescopic piston rod 4, or if an additional gear wheel is provided between the two gear wheels 20, 21 such that the first telescopic piston rod 4 and the additional telescopic piston rod 14 rotates in the same direction stress will build up in the additional telescopic piston rod 14, and a momentum will occur at the point where the additional telescopic piston rod 14 is secured in the housing 1. This unwanted momentum is however simply prevented by rotating the first telescopic piston rod 4 and the additional telescopic piston rod 14 in opposite directions.

The mating threads connecting the three parts 5, 6, 7 of the first telescopic piston rod 4 and the mating threads connecting the three parts 15, 16, 7 of the additional telescopic piston rod 14 has to be in a direction which will cause the distal end of both the first telescopic piston rod 4 and the distal end of the additional telescopic piston rod 14 to move in the distal direction inside the cartridge when the first part 5 of the first telescopic piston rod 4 is rotated.

Figure 4:
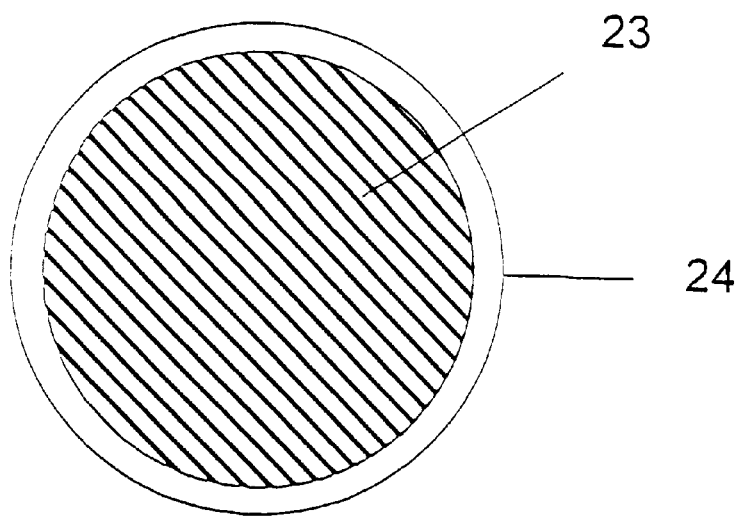
FIG. 4 Shows a cross-sectional view of the prior art medication delivery device.

FIG. 4 shows a cross-sectional view of the prior art medication delivery device shown in FIG. 3B in WO 97.00091. As can be seen the outside diameter of the outer bushing 23 is somewhat equal to the interior diameter of the cartridge 24. The outside diameter of the outer bushing protrudes into the housing1 of the medication delivery device, leaving no space for the remaining parts of the medication delivery device.

Figure 5:
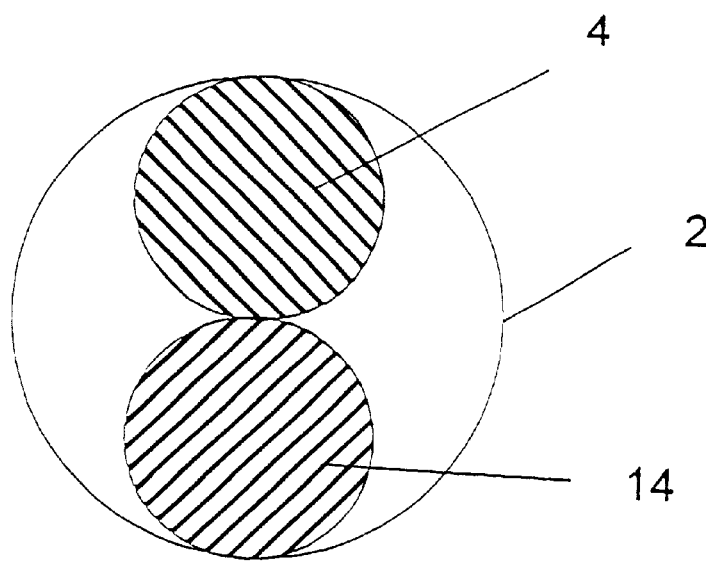
FIG. 5 Shows a cross-sectional view of the medication delivery device according to the present invention.

FIG. 5 shows a cross-sectional view of the medication delivery device of the present invention. Since both telescopic piston rods 4,14 are fitted into the same cartridge 2, the largest outside diameter of each telescopic piston rod 4,14 has to be substantially smaller than the interior diameter of the cartridge 2. Since the largest outside diameter of each telescopic piston rod 4,14 protrudes into the housing 1 a large amount of non-occupied space is available inside the housing 1 in comparison with the prior art medication delivery device.

Some preferred embodiments have been shown in the foregoing, but it should be stressed that the invention is not limited to these, but may be embodied in other ways within the subject-matter defined in the following claims.

All though the present invention has been described in relation to an injector type device the scope of the claims are not in any way limited to such an injector type device, but may e.g. also include a medication pump for continuous delivery of a liquid medication.

I claim:

1. A medication delivery device for delivering medicine or other fluent material to a mammal body, having a housing (1) accommodating a cartridge (2) containing an amount of said medicine, comprising:

an elastomeric piston (3) movable mounted in said cartridge (2), which elastomeric piston (3) is moved from a proximal end of said cartridge (2) towards a distal end of said cartridge (2) by rotating at least a part (5) of a first telescopic piston rod (4), which first telescopic piston rod (4) has a distal part (7) abutting said elastomeric piston (3) and a proximal part (5) rotatably mounted in said housing (1) and a plurality of parts (6) there between, said parts (5,6,7) being connected to each other by mating threads, drive means (8,9,10,11) for rotating said first telescopic piston rod (4), such that said elastomeric piston (3) moves forward inside said cartridge (2) and expels an amount of said medicine, and means preventing said elastomeric piston (3) from rotating when said part (5) of said first telescopic piston rod (4) is rotated, characterized in that said means preventing said elastomeric piston (3) from rotating when at least a part (5) of said first telescopic piston rod (4) is rotated comprises an additional telescopic piston rod (14) having a proximal end mounted in said housing (1) and a distal end abutting said elastomeric piston (3).

2. A medication delivery device according to claim 1, characterized in that said additional telescopic piston rod (14) is rotatably mounted in said housing (1).

3. A medication delivery device according to claim 1, wherein said additional telescopic piston rod (14) extends parallel to said first piston rod (4) inside said cartridge (2).

4. A medication delivery device according to claim 1, wherein said first telescopic piston rod (4) and said additional telescopic piston rod (14) are connected to each other through a synchronization gear (20, 21), such that both telescopic piston rods (4, 14) rotate with the same rotational speed, and wherein one of said telescopic piston rods (4, 14) is rotated by an electric motor (8) which drives one of said telescopic piston rods (4, 14) through a driving gear (9, 10, 11).

5. A medication delivery device according to claim 1, wherein said first telescopic piston rod (4) and said additional telescopic piston rod (14) each comprises three parts (5, 6, 7, 15, 16, 17) including a first part (5, 15) having an interior thread, a third part (7, 17) having an exterior thread, and an intermediate second part (6, 16) having an exterior thread mating said interior thread of said first part (5, 15) and an interior thread mating said exterior thread of said third part (7, 17).

6. A medication delivery device according to claim 5, wherein said first telescopic piston rod (4) and said first part (15) of said additional telescopic piston rod (14) are located at said proximal end of said cartridge (2), and wherein said third part (7) of said first telescopic piston rod (4) and said third part (17) of said additional telescopic piston rod (14) are movable towards said distal end of said cartridge (2).

7. A medication delivery device according to claim 5, wherein the direction of said threads of said first telescopic piston rod (4) and said additional telescopic piston rod (14) is such that said distal end of each telescopic piston rod (4, 14) travels in the same direction inside said cartridge (2) when one of said telescopic piston rods (4, 14) is rotated.

8. A medication delivery device according to claim 7, wherein said first telescopic piston rod (4) and said additional telescopic piston rod (14) rotate in the same direction.

9. A medication delivery device according to claim 7, wherein said first telescopic piston rod (4) and said additional telescopic piston rod (14) rotate in opposite directions.

10. A medication delivery device according to claim 1, wherein said first telescopic piston rod (4) at said distal end is connected to said distal end of said additional telescopic piston rod (14) through a circular plate (18) abutting said elastomeric piston (3) inside said cartridge (2).

* * * * *